United States Patent
Brekke et al.

(10) Patent No.: US 10,107,742 B2
(45) Date of Patent: Oct. 23, 2018

(54) METHOD AND SYSTEM FOR MONITORING THE QUALITY OF FLUIDS

(71) Applicant: Siemens Aktiengesellschaft, Munich (DE)

(72) Inventors: Endre Brekke, Trondheim (NO); Dmitry Dolgopyatov, Moscow (RU); Sandra Silke Jany, Trondheim (NO); Vitaly Malinin, Moscow (RU); Ivan Nikolin, Moscow (RU)

(73) Assignee: Siemens Aktiengesellschaft, Munich (DE)

( * ) Notice: Subject to any disclaimer, the term of this patent is extended or adjusted under 35 U.S.C. 154(b) by 159 days.

(21) Appl. No.: 14/897,751

(22) PCT Filed: Jun. 18, 2013

(86) PCT No.: PCT/RU2013/000510
§ 371 (c)(1),
(2) Date: Dec. 11, 2015

(87) PCT Pub. No.: WO2014/204335
PCT Pub. Date: Dec. 24, 2014

(65) Prior Publication Data
US 2016/0131575 A1    May 12, 2016

(51) Int. Cl.
*G01N 21/31* (2006.01)
*G01N 33/28* (2006.01)
*G01N 24/10* (2006.01)

(52) U.S. Cl.
CPC ............. *G01N 21/31* (2013.01); *G01N 24/10* (2013.01); *G01N 33/28* (2013.01); *G01N 33/2847* (2013.01); *G01N 33/2876* (2013.01)

(58) Field of Classification Search
CPC ............................... G01N 33/26; G01N 33/30
See application file for complete search history.

(56) References Cited

U.S. PATENT DOCUMENTS

| | | | |
|---|---|---|---|
| 5,818,731 A * | 10/1998 | Mittal | A47J 37/1266 702/22 |
| 6,268,727 B1 | 7/2001 | King et al. | |
| 6,633,035 B1 * | 10/2003 | Katagiri | G01N 21/3151 250/339.1 |
| 9,234,834 B2 * | 1/2016 | Van Mechelen | G01N 21/3504 |

(Continued)

FOREIGN PATENT DOCUMENTS

| | | |
|---|---|---|
| EP | 0816830 A2 | 1/1998 |
| GB | 2341685 A | 3/2000 |

OTHER PUBLICATIONS

Kozlov, Vladimir, and Alexander Turanov. "Transformer oil and modern physics." IEEE Transactions on Dielectrics and Electrical Insulation 19.5 (2012).*

*Primary Examiner* — Shawn Decenzo
(74) *Attorney, Agent, or Firm* — Cozen O'Connor

(57) ABSTRACT

A method and system for monitoring the quality of fluids, wherein comprising the different features of a fluid with at least two different methods are measured and a measure for the quality of the fluid is derived and/or a process of the fluid deterioration is identified by comparing the results of the measurements of the at least two different methods, where the methods includes at least one optical absorption measurement and at least one electron paramagnetic resonance measurement.

25 Claims, 3 Drawing Sheets

| Sample No. | Type of MIDEL ageing (measure for quality) | Turbidity in VIS range $T_U$ | Integral EPR signal $S_{EPR}$ |
|---|---|---|---|
| 1 and 6 | Not aged | Low L | Low L |
| 2 | With incompatible plastic | High H | Low L |
| 3 and 4 | Thermal aging with Nomex | Low L | High H |
| 5 | Fuse breakdown | Very High vH | Very High vH |

(56) References Cited

U.S. PATENT DOCUMENTS

| | | |
|---|---|---|
| 2005/0140368 A1 | 6/2005 | Freedman |
| 2008/0164874 A1 | 7/2008 | White et al. |
| 2009/0128144 A1 | 5/2009 | Freedman et al. |
| 2012/0022694 A1 | 1/2012 | Mohanty et al. |
| 2012/0133364 A1* | 5/2012 | White .................. G01N 24/08 |
| | | 324/316 |

* cited by examiner

FIG 3

| Sample No. | Type of MIDEL ageing (measure for quality) | Turbidity in VIS range $T_U$ | Integral EPR signal $S_{EPR}$ |
|---|---|---|---|
| 1 and 6 | Not aged | Low L | Low L |
| 2 | With incompatible plastic | High H | Low L |
| 3 and 4 | Thermal aging with Nomex | Low L | High H |
| 5 | Fuse breakdown | Very High vH | Very High vH |

METHOD AND SYSTEM FOR MONITORING THE QUALITY OF FLUIDS

CROSS-REFERENCE TO RELATED APPLICATIONS

This is a U.S. national stage of application No. PCT/RU2013/000510 filed 18 Jun. 2013.

BACKGROUND OF THE INVENTION

1. Field of the Invention The present invention relates to a method and a system using the method for monitoring the quality of fluids, comprising the measurement of different features of a fluid with at least two different methods and deriving a measure for the quality of the fluid and/or identifying a process of the fluid deterioration by comparing the results of the measurements of the at least two different methods.

2. Description of the Related Art The quality monitoring of fluids is particularly important for defect free, continuous operation of transformers, switchgears, fuses and other equipment, such as in power grids. Among other things, fluids are used as transformer oil or dielectric fluid in electrical equipment, and are usually highly-refined mineral oils or synthetic esters, which are stable at high temperatures and have excellent electrical insulating properties. The quality of the fluids plays an important role for the proper function of the equipment comprising the fluid. The quality changes due to changes in properties of these fluids, such as acidity, water content or the concentration of free radicals. The natural degradation can be accelerated by elevated temperature and/or pressure, or by chemical reactions with other components, such as like plastic parts.

The qualities of the fluids and degradation have to be monitored to identify and forecast the ageing process of used fluids and the entire apparatus/construction. The fluids, particularly liquids, are used to insulate, suppress corona and arcing, and to serve as a coolant, such as in oil-filled transformers, some types of high voltage capacitors, fluorescent lamp ballasts, and sortie types of high voltage switches and circuit breakers. A proper function of a used fluid and of the apparatus is only assured with a certain level of fluid quality. In subsea applications the quality has to be remotely monitored.

A low fluid quality can lead to a breakdown of an apparatus and thereby destroy equipment. To prevent this, fluids have to be replaced when they degrade below a certain, predefined quality level. The degradation below the quality level is identified by monitoring the fluid, particularly liquid. A continuous monitoring reduces the time to replace degraded fluids and the risk of failure.

A sensing technique for the monitoring of a fluid has to be reliable, miniaturized, insensitive to electromagnetic noise, and in some oases able to withstand harsh environments, i.e., high pressure of up to 300 bar, such as in subsea applications and high temperature.

From the 1990s, on-line monitoring particularly of transformers has become increasingly popular tending to reduce the number of time-based diagnostic operations, where in some cases equipment has to be shut down. The most common methods known from the state of the art, both monitoring and diagnostics methods are:

Dissolved gas analysis (DGA):
  Multiple gas sensor;
  Hydrogen sensor;
  Individual gas sensors;
Partial discharge (PD) monitoring:
  Glass fiber rods;
  Electrical (RF coils);
  Electrical (phase impulse current);
  Acoustic;
  Via DGA (Hydrogen);
Cellulose and oil moisture content:
  Dielectric response analysis;
  Capacitive probes;
  Fiber optical;
  Karl Fischer titration;
Degree of polymerization (DP):
  Paper samples;
  Furanic compounds analysis;
Spectroscopy/Transparency:
  Ultraviolet/visible—UV/VIS;
  NIR;
  MIR;
  Integral attenuation in a broad spectrum range;
  Visual evaluation;
Acidity tests;
Dielectric strength tests;
Resistivity tests.

DGA utilizes the measurement of concentrations of $H_2$, $CH_4$, $C_2H_6$, $C_2H_4$, $C_2H_2$/CO and $CO_2$ for transformer fault detection. With respect to remote condition monitoring, DGA based systems implement either gas chromatography or photo-acoustic spectroscopy. Both techniques require dissolved gas separation from oil, which is not feasible under high pressure.

PD activity monitoring is a convenient tool to detect degradation of the transformer insulation. Nevertheless, it does not provide any information on dielectric fluid contaminants composition.

Karl Fischer titration, DP measurement with paper samples, acidity test and dielectric strength test are not feasible for in-situ implementation. Dielectric response analysis requires transformer shut-down. Capacitive moisture sensors withstanding pressures up to 200 bar are known, but this is often not sufficient to meet requirements.

MIR spectroscopy is a standardized laboratory technique for inspecting insulating oil but it is not specialized for aging mechanism determination. The technique is more appropriate for lubricants.

Separately, none of the techniques can provide enough data for fluid condition monitoring and fluid aging mechanism determination. Many of the above-listed technologies are intended for laboratory use only.

SUMMARY OF THE INVENTION

It is therefore an object of the present invention to provide a method and a system using the method to determine the quality of a fluid reliably, particularly the aging of the fluid. A further object is to be able to continuously and/or remotely control the quality of a fluid to be able to change the fluid below a quality level to guarantee the proper function of equipment comprising and/or using the fluid. A further object is to provide a method and system allowing the determination and discrimination between the mechanisms of fluid aging, which mechanisms correspond to the types of failure experienced particularly by equipment like a transformer.

These and other objects and advantages are achieved in accordance with the invention by a system and method for monitoring the quality of fluids in accordance with the present invention which comprises the measurement of different features of a fluid with at least two different methods and deriving a measure for the quality of the fluid by comparing the results of the measurements of the at least two different methods. The methods include at least one optical absorption measurement and at least one electron paramagnetic resonance measurement (EPR).

With one method alone, as known from the state of the art, it is not possible to determine the quality level and aging mechanism of a fluid reliably. Particularly, a proper function of equipment like transformers in the whole range of working Conditions and environments cannot be guaranteed using just one method alone. With the combination of at least one optical absorption measurement and at least one electron paramagnetic resonance measurement (EPR), it is possible to derive the quality of the fluid as a measure, for example, of aging of the fluid, particularly chemical aging, and the aging mechanism. The change of acidity, water content, and/or of free radicals concentration can be determined.

The reliable determination of the quality enables the fluid to be exchanged as soon the quality is below a predefined quality level. For equipment using the fluid, a proper function without the risk of failure due to the low quality of fluid can be guaranteed.

The determination of quality can be reliably achieved for a dielectric liquid and/or oil, particularly a highly-refined mineral oil or synthetic ester, or a mixture comprising a dielectric liquid and/or oil as fluid. One method alone is unable able to successfully derive reliably the quality level of these liquids and the aging mechanism. Only in combination is it possible to identify the degree of deterioration of the fluid and the mechanism of its aging. Optical absorption measurements, particularly within the visible spectral range (VIS), provide information on dielectric fluid turbidity and color. Optical absorption measurements from the near infrared range (NIR) to the middle infrared range (MIR) can also provide information about turbidity and specific impurities present particularly in oil.

According to theory, the conductivity and dissipation factor tan δ of the fluid is dependent on colloidal structures present in the fluid. The colloidal structures are formed due to the interaction between paramagnetic centers (PMC) with diamagnetic molecules of aromatic, naphthenic and paraffinic hydrocarbons. The PMC are free radicals and metals., i.e., copper and iron. Previous research has found a correlation between PMC concentration in oil and tan δ.

Optical and EPR integral signals can show, particularly for dielectric liquids and/or oil, no or only little correlation with each other because they depend on different features of the fluid, hence providing independent and complementary information about fluid condition and aging mechanism. In combination of both methods, aging with common mechanisms, is reliably detectable.

In combination, optical and EPR measurements are able to provide measures, evaluated together allowing a determination of the quality level and aging of a fluid, particularly a liquid like oil.

The measurements can be made remotely. This also allows the ability to get information about the quality of a fluid in equipment that is hardly accessible. In contrast to measurements in a laboratory, it allows a continuous monitoring of the fluid quality. The determination of fluid quality can also occur under extreme conditions, particularly under high pressure. The measurements with the at least two different methods can be made at the same time or in short intervals following each other. It can also be made in a closed system, without opening the system. So sealed systems can be kept closed and, for example, contamination can be avoided or pressure can be kept at a high level.

The fluid can be comprised by a power grid unit, particularly a transformer and/or switchgear and/or a VSD. These components are of ten distributed in a large area in the countryside and/or city, and a remote measurement and determination of liquid quality, to guarantee a proper function can save effort and costs.

The EPR signal and the absorption in VIS range can be measured in combination, particularly in parallel at the same time. The EPR signal can be measured particularly as an integral value and/or as a spectrum. The absorption can be measured particularly in a fixed range of wavelength as integral value and/or as spectrum, and/or measured in transmission and/or as turbidity and/or as change in color. The details of measurement depend among others on the fluid, the equipment the fluid is used in and the quality level to be determined.

A measure for quality is derived comparing the measured values of the at least two different methods with standard values, particularly identifying a low quality with at least one of the measured values being higher or lower, depending on the method used, than the standard value. If the low quality value is reached or the value falls below a standard value, a signal/information can be transmitted to a controller, for example, in order to exchange the fluid manually or automatically or to execute other particular predefined actions.

An acceptable quality for use can be identified with both values being lower or higher, higher particularly for transmission measurements, than a standard value, particularly the turbidity in VIS range and the integral EPR signal below a standard value, and a necessary exchange of fluid is identified with at least one or both of the measured values being higher than the standard value.

The measurement can occur under high pressure conditions, particularly with a pressure higher than 200 bar. Also measurements in other extreme conditions such as low or high temperature, acid or corrosive environments, are possible.

It is also an object to provide a system in accordance with the present invention that can perform monitoring in accordance with the disclosed embodiments of the method, particularly comprising a power grid unit with at least one device for an optical absorption measurement and at least one device for an electron paramagnetic resonance measurement EPR.

In an embodiment, the system comprises particularly a monitored unit, for instance a transformer, a switchgear and/or a variable speed drive (VSD).

In another embodiment, the system comprises a fluid particularly in a closed container and with the at least one device for an optical absorption measurement and the at least one device for an electron paramagnetic resonance measurement EPR within or at/in close contact with the container.

In a further embodiment, the system comprises a device to remote control and/or analyze the measured data, particularly to compare the value of the at least one device for an optical absorption measurement and the value of the at least one device for an electron paramagnetic resonance measurement EPR with standard values and to derive the quality of liquid from a combination of compared values. A device to view measurement results and/or necessary actions depending on the results can be provided.

The advantages of the system are similar to advantages of the method for monitoring the quality of fluids previously described. Features can be used in connection or individually.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The present invention is further described hereinafter with reference to illustrated embodiments shown in the accompanying drawings, in which:

FIG. 3 illustrates the method in accordance with the present invention, deriving a measure for the quality of a fluid and aging mechanism by comparing the results of the measurements of FIGS. 1 and 2.

DETAILED DESCRIPTION OF THE EXEMPLARY EMBODIMENTS

Figure 1:
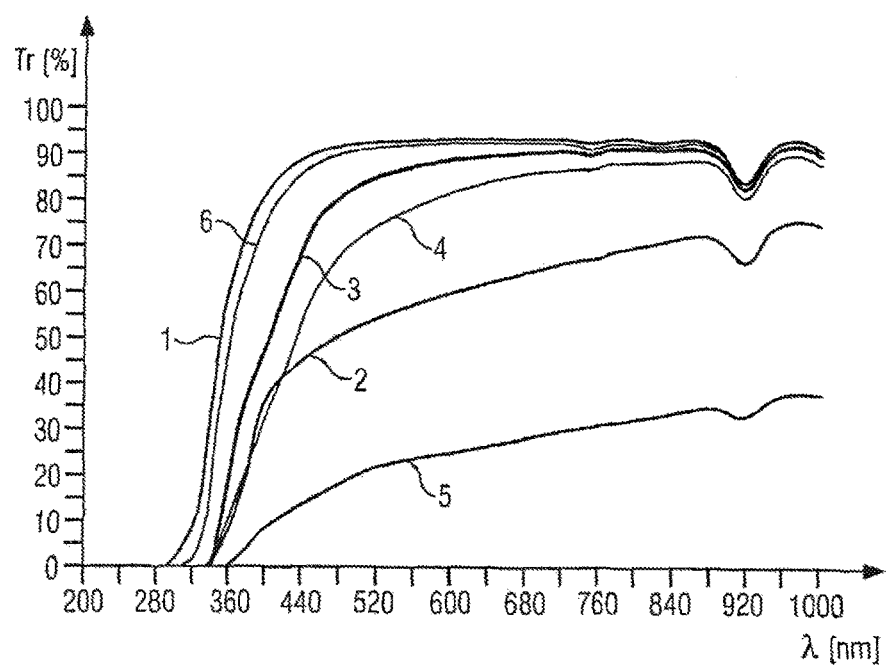
FIG. 1 illustrates a graphical plot of data from an optical absorption measurement.

In FIG. 1 an optical absorption measurement within visible spectral range VIS for a fluid Midel° 7131 is shown. Midel° 7131 is a liquid for oil-filled transformers and consists of a synthetical ester. Midel° 7131 is fire and environmentally safe. In non deteriorated, non aged stage, it is transparent, with a bit of yellow color.

In transmission spectra of FIG. 1, the transmission in percent %, depending on wavelength λ in nm in the spectral UV-VIS range is shown. Sample 1 and 6 are non aged, not deteriorated. Midel° 7131. Sample 1 is a more color less sample and sample 6 is of a bit more yellow color manually viewed. Both samples 1 and 6 show a high transmission in % in the UV-VIS spectra.

Samples 3 and 4 are liquid Midel° 7131 aged thermally, in contact with Nomex° at elevated temperatures. The aging has been performed for 2000 hours (sample 3) and 4000 hrs (sample 4), both at 150° C. Nomex° is a flame-resistant meta-armid polymer material. Nomex° can be produced in the form of paper sheets, particularly used for electrical insulation. As seen in FIG. 1 the transmission $T_r$ of samples 3 and 4 is lower than that of imaged samples 1 and 6 in the entire UV-VIS range. The visible color of sample 3 is strong yellow and the visible color of sample 4 is strong brown/red.

Sample 2 is liquid Midel° 7131 aged with incompatible plastic. The aging has been performed for 3 months at 105° C. As seen in FIG. 1, the transmission $T_r$ of sample 2 is lower than the transmission $T_r$ of samples 1, 6, 3 and 4 nearly in the entire spectral UV-VIS range. Only sample 4 shows a slightly smaller or substantially the same transmission in a range of wavelength below 420 nm. The color of sample 2 is cloudy/milky yellow.

Sample 5 is liquid Midel° 7131 aged by a fuse breakdown. As seen in FIG. 1 the transmission $T_r$ of sample 2 is lower than the transmission of the other samples 1 to 4 and 6 in the entire spectral UV-VIS range. The visible color of sample 5 is dark black.

Alternative to transmission $T_r$ curves in the UV-VIS range, the integral value of the area below the curve can be used as a result of the optical absorption measurement for evaluation of the quality of the fluid, particularly liquid. The information and result, is the same as described before for the transmission $T_r$, dependent on wavelength A curves in the UV-VIS range.

The light absorption within visible spectral range UV-VIS, as shown in FIG. 1, provides information on dielectric fluid turbidity and color. With this information, the optical absorption and/or turbidity can be measured either in the VIS or NIR range or in both ranges and/or in another wavelength range. In the example of FIG. 1 only the data on VIS range turbidity are shown for the sake of simplicity.

Figure 2:
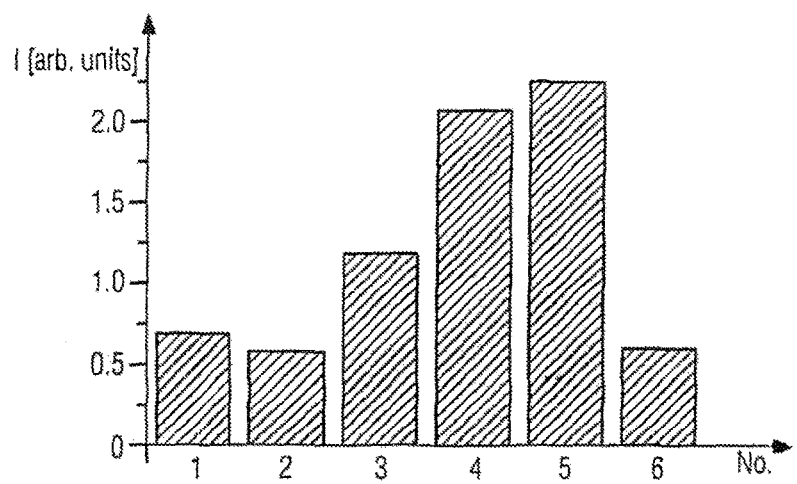
FIG. 2 illustrates a bar chart of data of an electron paramagnetic resonance measurement EPR.

In FIG. 2, Electron Paramagnetic Resonance (EPR) measurements on the same samples 1 to 6 of FIG. 1 are shown. The EPR signal $S_{EPR}$ is given in arbitrary units, depending on the sample number No. As can be seen in FIG. 2, the sample 5, liquid Midel° 7131 aged by a fuse breakdown, shows very high vH EPR signal intensity I. It is the highest EPR signal intensity I of all measured samples 1 to 6.

Samples 3 and 4, liquid Midel° 7131 aged thermally in contact with Nomex° at elevated temperatures, show a high H EPR signal $S_{EPR}$. The EPR signal $S_{EPR}$ intensity I is lower than the signal intensity I of sample 5, but higher than the signal intensity I of samples 1, 2 and 6.

Samples 1 and 6, unaged liquid Midel° 7131, show low L EPR signal $S_{EPR}$ intensity I.

Also sample 2, liquid Midel° 7131 aged with incompatible plastic, shows low L EPR signal $S_{EPR}$ intensity I. It is even slightly lower than the intensity I of samples 1 and 6. Samples 1, 2 and 6 show all three low L intensity I in EPR signal $S_{EPR}$ measurements. It is not possible to distinguish aging from no aging alone on EPR measurements.

In FIG. 3 a schema summarizing and comparing the measurements of transmission spectra of FIG. 1 in the spectral UV-VIS range and Electron Paramagnetic Resonance EPR measurements of FIG. 2 is shown. The results in form of qualitative information about turbidity $T_u$ in VIS range of FIG. 1, compared to results in form of qualitative information about the integral EPR signal $S_{EPR}$ of FIG. 2 are given.

As evident from FIG. 3, fluid without deterioration can be distinctly identified and distinguished from aged fluid by comparing measured results of optical UV-VIS in combination with EPR measurements. A measure for the quality of the fluid is given in the form of the information aged or not aged by comparing the results of the measurements of the two different, methods optical UV-VIS and EPR measurement. With values for turbidity $T_u$ in VIS range low L and EPR signal $S_{EPR}$ low L the quality of fluid is good, and there is no requirement to change and/or exchange the fluid to guarantee a proper functional operation of equipment using the turbidity $T_u$. With values for turbidity $T_u$ in VIS range low L and EPR signal $S_{EPR}$ high H, or values for turbidity $T_u$ in VIS range high H and EPR signal $S_{EPR}$ low L, or both values high K or very high vH, the quality of fluid is not good and must be further checked, changed and/or exchanged to guarantee a proper functional operation of equipment using the fluid. Further, the aging mechanism, see FIG. 3 second column, can be determined and distinguished.

Only in combination is reliable information provided by the two methods about the quality of the liquid, particularly with respect to aging/deterioration, and the aging mechanism. With one method, it is not possible to reliably evaluate the quality and the need for action with respect to aging/deterioration of the liquid and its changing and/or exchange. The aging mechanism determined also provides information on the processes that may lead to its failure within equipment like transformers.

Both methods, optical and EPR measurements can be performed remotely. This enables measurements and a quality evaluation in harsh environments, and/or a simultaneous monitoring of properties of a fluid particularly continuously, and/or online, such as with a computer. The disclosed embodiments offer an interpretation technique providing fluid deterioration scenario and reason identification.

In the special case of FIG. 3, the measure for the quality of the fluid by comparing the results of the measurements of the two different methods, the optical and the Electron Paramagnetic Resonance SER measurements, is (i) low L VIS and low L EPR signals combination indicates no deterioration of the fluid, (ii) high H VIS and low L EPR signals combination indicates deterioration of the fluid by incompatible plastic, (iii) low L VIS and high H EPR signals combination indicates deterioration of the fluid with Nomex° at high temperatures, and (iv) high R VIS and high H EPR signals combination indicates deterioration of the fluid by a fuse breakdown.

For other applications and fluids, the specific measure and the scheme can be different. However, a clear determination of the quality of liquid is possible with a combination of the at least two methods also in other applications and for other liquids. The methodology illustrated in FIG. 3 is merely an example for the method for monitoring the quality of fluids in accordance with the present invention. The methodology of FIG. 3 can be used as described before, in combination with different features described before and in combination with conventional methods and features. The optical absorption (transparency) measurements can occur within a specific bandwidth or bandwidths of UV-VIS spectra. Either the integral optical signal or optical spectra can be used or both. For EPR signal acquisition, the integral signal and/or spectra can also be used. The data analysis and discrimination between several predetermined aging mechanisms can be performed manually or automatically, particularly after transmitting data from a remote measurement. NIR-MIR data can be used both on turbidity and on specific impurities present in the fluid, such as oil.

Even when the methodology of deterioration scenario determination for different fluids is different in detail, it is possible to monitor and interpret optical and EPR signals at the same time for all fluids. This combination of optical and EPR monitoring provides a good basis for the fluid ageing scenario interpretation. This offers a safe and reliable tool for quality monitoring of, for example, isolating liquids for remote equipment, such as oil in transformers. The mutual optical and EPR data interpretation allows conclusions on the specific processes taking place in a fluid.

Advantages of the present invention are, inter alia, the possibility to remotely monitor fluids properties without intervention to equipment working regime due to installed optical and EPR measurement sensors/systems, and more precisely to identify events such as equipment break down, compared with methods merely using optical or BEE signals alone, by analysing the reasons of the fluid deterioration. Equipment ageing can be calculated with the help of monitoring data, so as to avoid failures and expensive repairs of equipment. Equipment faults can be detected in their infancy, enabling fast remedial response. There is an easy adaptation of the proposed methodology for a variety of constructions and equipments. The technology can be implemented in high pressure conditions, for example in subsea equipment.

Figure 4:
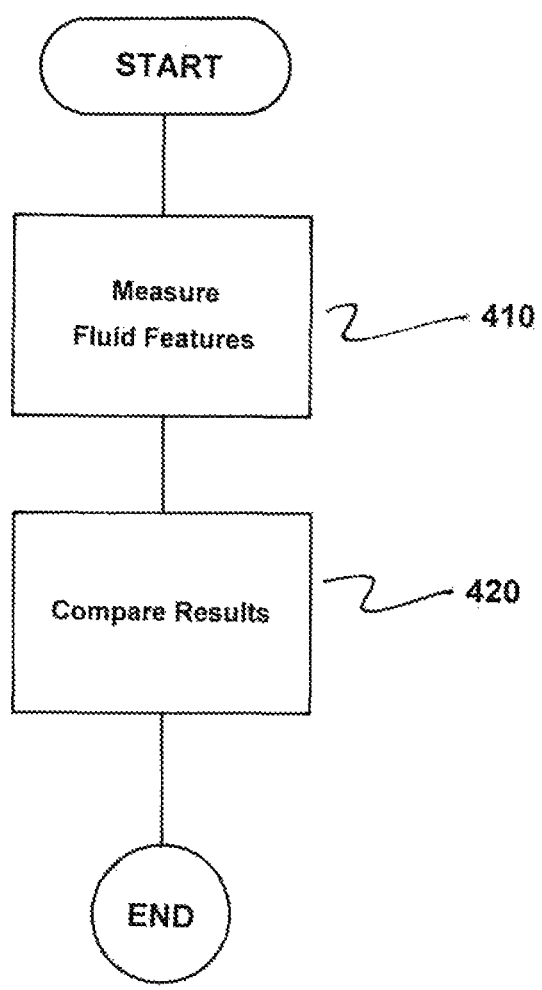
FIG. 4 is flowchart of the method in accordance with the invention.

FIG. 4 is a flowchart of a method for monitoring quality of fluids. The method comprises measuring different features of a fluid with at least two different methods, as indicated in step 410.

Next, the results of the measurements of at least two different methods are compared to at least one of (i) derive a measure for a quality of the fluid and (ii) identify a process of the fluid deterioration, as indicated in step 420. In accordance with the method of the invention, at least two methods comprise at least one optical absorption measurement and at least one electron paramagnetic resonance measurement (EPR).

While there have been shown, described and pointed out fundamental novel features of the invention as applied to a preferred embodiment thereof, it will be understood that Various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for monitoring quality of fluids, comprising:
   measuring different features of a fluid with at least two different methods comprising at least a first measurement method and at least a second measurement method which are implemented simultaneously; and
   comparing results of the measurements of the at least two different methods comprising at least the first measurement method and at least the second measurement method which are implemented simultaneously to at least one of (i) derive a measure for a quality of the fluid and (ii) identify a process of the fluid deterioration;
   wherein the first and the second measurement methods each comprise at least one optical absorption measurement and at least one electron paramagnetic resonance measurement.

2. The method according to claim 1, wherein the method is implemented to identify aging of the fluid in connection with plastic or other incompatible materials.

3. The method according to claim 2, wherein the aging comprises chemical aging.

4. The method according to claim 3, wherein the chemical aging comprises at least one of a change of acidity, water content and free radicals concentration.

5. The method according to claim 2, wherein the aging comprises at least one of thermal aging and aging over time.

6. The method according to claim 1, wherein the fluid is at least one of (i) a dielectric liquid and (ii) an oil.

7. The method according to claim 2, wherein the fluid is at least one of (i) a dielectric liquid and (ii) an oil.

8. The method according to claim 6, wherein the fluid is one of (i) a highly-refined mineral oil or synthetic ester, and (ii) a mixture comprising at least one of a dielectric liquid and an oil.

9. The method according to claim 7, wherein the fluid is one of (i) a highly-refined mineral oil or synthetic ester, and (ii) a mixture comprising at least one of a dielectric liquid and an oil.

10. The method according to claim 1, wherein the measurements are performed at least one of (i) remotely, (ii) under high pressure and (iii) in a closed system.

11. The method according to claim 1, wherein the fluid is enclosed by a power grid unit.

12. The method according to claim 11, wherein the power grid unit is at least one of a transformer, a switchgear and a variable speed drive.

13. The method according to claim 1, further comprising:
at least one of (i) determining a fluid deterioration process and (ii) discrimination between fluid deterioration processes.

14. The method according to claim 1, wherein at least one of (i) a electron paramagnetic resonance measurement signal comprising at least one of an integral value and spectrum, (ii) an absorption in at least one of a visible spectral range and another range comprising a fixed range or several ranges of wavelength as at least one of an integral value and spectrum, measured in transmission, as turbidity and change in color, is measured in combination.

15. The method as claimed in claim 14, wherein the measurements are performed in parallel at the same time.

16. The method according to claim 1, wherein a measure for quality is derived by comparing the measured values of the at least two different methods comprising at least the first measurement method and at least the second measurement method with standard values; and wherein a low quality is identified when at least one of the measured values is higher or lower than the standard value.

17. The method according to claim 16, wherein an acceptable quality for use is identified with both values lower than a standard value, and a necessary exchange of fluid is identified with at least one or both of the measured values being higher than the standard value.

18. The method according to claim 17, wherein the standard value comprises a turbidity in a visible spectral range and an integral of an electron paramagnetic resonance measurement signal.

19. The method according to claim 1, wherein the measuring occurs in high pressure conditions.

20. The method according to claim 19, wherein the pressure is higher than 200 bar.

21. A system comprising:
a power grid unit having at least one device for an optical absorption measurement; and
at least one device for an electron paramagnetic resonance measurement (EPR), the system being monitored by:
measuring different features of a fluid with at least two different methods comprising at least a first measurement method and at least a second measurement method which are implemented simultaneously; and
comparing results of the measurements of the at least two different methods comprising at least the first measurement method and at least the second measurement method which are implemented simultaneously to at least one of (i) derive a measure for a quality of the fluid and (ii) identify a process of the fluid deterioration;
wherein the first and the second measurement methods each comprise at least one optical absorption measurement and at least one electron paramagnetic resonance measurement.

22. The system according to claim 21, further comprising:
at least one of a transformer, a switchgear and variable speed drive.

23. The system according to claim 21, further comprising:
a fluid in a closed container;
wherein the at least one device for the optical absorption measurement and the at least one device for the electron paramagnetic resonance measurement are within or at the container.

24. The system according to claim 22, further comprising:
a fluid in a closed container;
wherein the at least one device for the optical absorption measurement and the at least one device for the electron paramagnetic resonance measurement are within or at the container.

25. The system according to claim 21, further comprising:
a device to at least one of (i) remotely control the measured data and (ii) analyze the measured data;
wherein the device compares a value obtained by the at least one device for the optical absorption measurement and the value obtained by the at least one device for the electron paramagnetic resonance measurement with standard values and derives a quality of the fluid from a combination of compared values.

* * * * *